United States Patent
Niu (10) Patent No.: US 9,955,556 B2
(45) Date of Patent: Apr. 24, 2018

(54) METHOD AND SYSTEM FOR CONTROLLING LIGHTING EFFECT ON MOBILE DEVICES

(71) Applicant: Zhuochao Niu, West Covina, CA (US)

(72) Inventor: Zhuochao Niu, West Covina, CA (US)

( * ) Notice: Subject to any disclaimer, the term of this patent is extended or adjusted under 35 U.S.C. 154(b) by 0 days.

(21) Appl. No.: 15/598,667

(22) Filed: May 18, 2017

(65) Prior Publication Data
US 2018/0092188 A1 Mar. 29, 2018

Related U.S. Application Data

(60) Provisional application No. 62/401,593, filed on Sep. 29, 2016.

(51) Int. Cl.
| | | |
|---|---|---|
| *H05B 37/02* | (2006.01) |
| *H04M 1/02* | (2006.01) |
| *H04W 24/00* | (2009.01) |
| *H04W 84/18* | (2009.01) |
| *H04W 4/08* | (2009.01) |
| *H04W 4/02* | (2018.01) |
| *G06Q 10/02* | (2012.01) |
| *G05B 19/042* | (2006.01) |
| *G05B 19/12* | (2006.01) |

(52) U.S. Cl.
CPC ....... *H05B 37/0227* (2013.01); *G05B 19/042* (2013.01); *G05B 19/124* (2013.01); *G06Q 10/02* (2013.01); *H04M 1/0214* (2013.01); *H04W 4/02* (2013.01); *H04W 4/08* (2013.01); *H04W 24/00* (2013.01); *H04W 84/18* (2013.01); *G05B 2219/23039* (2013.01)

(58) Field of Classification Search
CPC .. H05B 37/227; H04M 1/0214; H04W 24/00; H04W 84/18; H04W 4/08; H04W 4/02; G06Q 10/02; G05B 19/042; G05B 19/124
See application file for complete search history.

(56) References Cited

U.S. PATENT DOCUMENTS

| | | | |
|---|---|---|---|
| 6,348,648 B1 * | 2/2002 | Connick, Jr. ........ | G09B 15/023 84/477 R |
| 9,094,489 B1 * | 7/2015 | Groenjes ............. | H04M 1/0214 |
| 2005/0113075 A1 * | 5/2005 | Haberman .............. | H04W 4/02 455/414.2 |
| 2014/0113598 A1 * | 4/2014 | Conti .................... | G06F 3/1446 455/414.1 |

(Continued)

*Primary Examiner* — Daniel Walsh
(74) *Attorney, Agent, or Firm* — Che-Yang Chen; Law Offices of Scott Warmuth (57) ABSTRACT

In one aspect, a system for controlling lighting effect on a mobile device may include at least a 3C client end having at least one mobile device, at least a light effect control (LEC) end, and a server. Through a network, the server can connect with the 3C client end and the LEC client end. In one embodiment, the server can connect to a plurality of 3C client ends concurrently, but only enables a single LEC client end to connect thereto. The server has a database which is configured to separately store data of the 3C client ends, the LEC client ends and communications therebetween. Each of the venues has a plurality of preset flash lighting patterns for the 3C client ends, and the venue comprises its identified data and service data which are individually saved in the database and can be retrieved once the server is activated.

6 Claims, 12 Drawing Sheets

(56) References Cited

U.S. PATENT DOCUMENTS

| | | | | |
|---|---|---|---|---|
| 2014/0164149 A1* | 6/2014 | Huff | ................... | G06Q 30/0601 |
| | | | | 705/14.73 |
| 2015/0012308 A1* | 1/2015 | Snyder | ................... | G06Q 10/02 |
| | | | | 705/5 |
| 2016/0073484 A1* | 3/2016 | Czapla | ................... | H04H 20/61 |
| | | | | 315/323 |
| 2017/0048951 A1* | 2/2017 | Huang | ............... | H05B 37/0272 |
| 2017/0135165 A1* | 5/2017 | Lu | ........................ | H05B 33/086 |

* cited by examiner

METHOD AND SYSTEM FOR CONTROLLING LIGHTING EFFECT ON MOBILE DEVICES

FIELD OF THE INVENTION

The present invention relates to a method and system for modulating lighting effect on mobile devices, and more particularly to a method and system for controlling lighting effect on mobile devices especially in a concert or party.

BACKGROUND OF THE INVENTION

For enlivening the atmosphere, glow sticks are frequently used at a party or a concert. Generally, the glow stick has a brittle inner container, and a flexible outer container covers outside thereof. Moreover, the glow stick may include a suitable fluorescent dye retained therein. Two preferable chemicals are respectively kept inside the two containers, and when a user flexes the outer container, the two chemicals are configured to be mixed so as to initiate the chemical reaction and emit at least a preferable light thereby providing embellishment at the party or concert.

However, conventional glow sticks are disadvantageous because: (i) the glow stick cannot be turned off once activated, and it only can glow for a short period of time, which limits its applicability; and (ii) as mentioned above, the glow stick can only emit the light for a short period of time and cannot be reused, which is neither cost-effective nor environmentally friendly. Thus, more and more people use the flash lights on their cellular phones in a party or concert as glow sticks. However, the flash light on the cell phone is monotonous because it can only generate very limited types of lights. Also, the flash light is control by each person in the party or concert, so it is difficult to synchronize the lights to generate a better lighting effect. Therefore, there remains a need for a new and improved design for a system to control lighting effect on mobile devices to overcome the problems presented above.

SUMMARY OF THE INVENTION

In one aspect, a system for controlling lighting effect on a mobile device may include at least a 3C client end having at least one mobile device, at least a light effect control (LEC) end, and a server. In one embodiment, through a network, the server is configured to connect with the 3C client end and the LEC client end. In another embodiment, the server is configured to connect to a plurality of 3C client ends concurrently, but only enables a single LEC client end to connect thereto. The server has a database which is configured to separately store data of the 3C client ends, the LEC client ends and communications therebetween. Moreover, each of the venues has a plurality of preset flash lighting patterns for the 3C client ends, and the venue comprises its identified data and service data which are individually saved in the database and can be retrieved once the server is activated. It is noted that different venues have different maximum acceptable numbers of the 3C client ends, depending on the size, type or pattern of venue. In one embodiment, the lighting effect controlling system in the present invention may have two types of communication data, which are register data and flash data. The register data are configured to describe different status of a client's register, and the client is can be the 3C client end or the LEC client end. The flash data may include different colors, frequencies and venue theme effects. It is noted that the communication data between the server and the 3C client end may have different formats from the communication data between the server and the LEC client ends.

Each of the venues cooperating with the lighting effect controlling system has an individual QR code which can be scanned by the 3C client end, and each of QR codes has a corresponding venue's ID. When a 3C client end scans a QR code of a designated venue, the server is configured to receive a register data corresponding to a venue ID (the QR code) sent from the 3C client end. In one embodiment, a register protocol of the 3C client end comprises a register and a venue ID. In one embodiment, in the designated venue, the server is configured to connect to only one LEC client end, and the LEC client end has different profiles provided by a system developer including a venue's ID and a confirmed password. The LEC client end can connect to the server by clicking at least a designated button on a panel of the LEC client end, and the LEC client end is configured to send register data to the server according to the profiles thereof. In one embodiment, a register protocol of the LEC client end may include a register, a venue ID and a password.

After connecting with the server, the 3C client end may not send further data to the server before next connection, and may only receive data sent from the server so as to check selected flash effect including colors, frequencies, and venue theme effects. It is noted that when sending the mentioned data of colors, frequencies and venue theme effects, the server is configured to ensure the independence between different venues and prevent mutual interference. In one embodiment, a data protocol of the 3C client end may include certain types of data including different colors, tempos, and venue theme effects. After connecting with the server, the LEC client end may not receive further data from the server before next connection, and may only send out data to the server. In one embodiment, the LEC client end is configured to send the designated colors, frequencies, venue theme effects to the connected 3C client end through the server. In another embodiment, a data protocol of the LEC client end may include certain types of data including colors, tempos, venue theme effects, a venue ID, and a password.

In one embodiment, the 3C client end, the LEC client end and the server are independently operated, and the server is configured to synchronize with the 3C client end or the LEC client end only when receiving the register data to achieve high concurrency and stability. As a result, the server is configured to have high processing speed when conducting and/or receiving a large amount of data. The server may further include a color flash data buffer system which is configured to enable the 3C client end and the LEC client end to register at any time. More specifically, the 3C client end or the LEC client is configured to connect to the server in a random order under a condition that a single venue is only connected and controlled by a single LEC client end at one time. Moreover, the server is configured to keep the latest connection of the LEC client end at a single venue; i.e. once a new LEC client end is connected to the server at the same venue, the current LEC client end is configured to be terminated and disconnected with the server.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

Figure 1:
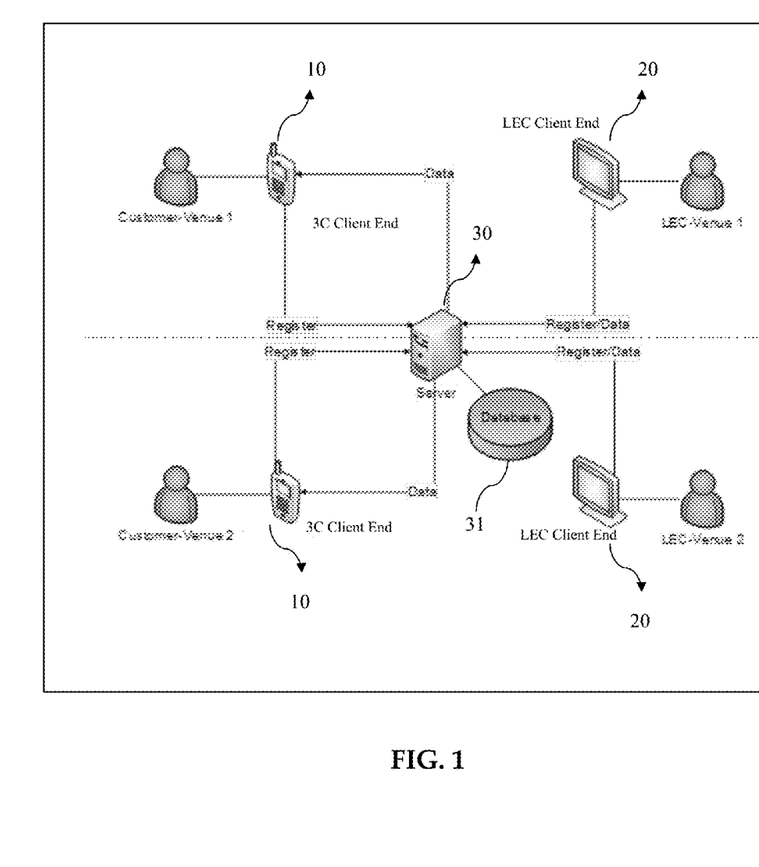
FIG. 1 is a schematic view of the connection and communication of the 3C client end, the LEC client end and the server in the present invention.

In order to further understand the goal, characteristics and effect of the present invention, a number of embodiments along with the drawings are illustrated as following:

In one aspect, referring to FIG. 1, a system for controlling lighting effect on a mobile device may include at least a 3C client end (10) having at least one mobile device, at least a light effect control (LEC) client end (20), and a server (30). In one embodiment, through a network, the server (30) is configured to connect with the 3C client end (10) and the LEC client end (20). In another embodiment, the server (30) is configured to connect to a plurality of 3C client ends (10) concurrently, but only enables a single LEC client end (20) to connect thereto. The server (30) has a database (31) which is configured to separately store data of the 3C client ends (10), the LEC client ends (20) and communications therebetween. Moreover, each of the venues has a plurality of preset flash lighting patterns for the 3C client ends (10), and the venue comprises its identified data and service data which are individually saved in the database (31) and can be retrieved once the server (30) is activated. It is noted that different venues have different maximum acceptable numbers of the 3C client ends (10), depending on the size, type or pattern of venue. In one embodiment, the lighting effect controlling system in the present invention may have two types of communication data, which are register data and flash data. The register data are configured to describe different status of a client's register, and the client is can be the 3C client end (10) or the LEC client end (20). The flash data may include different colors, frequencies and venue theme effects. It is noted that the communication data between the server (30) and the 3C client end (10) may have different formats from the communication data between the server (30) and the LEC client ends (20).

Each of the venues cooperating with the lighting effect controlling system has an individual QR code which can be scanned by the 3C client end (10), and each of QR codes has a corresponding venue's ID. When a 3C client end (10) scans a QR code of a designated venue, the server (30) is configured to receive a register data corresponding to a venue ID (the QR code) sent from the 3C client end (10). In one embodiment, a register protocol of the 3C client end (10) comprises a register and a venue ID. In one embodiment, in the designated venue, the server (30) is configured to connect to only one LEC client end (20), and the LEC client end (20) has different profiles provided by a system developer including a venue's ID and a confirmed password. The LEC client end (20) can connect to the server (30) by clicking at least a designated button on a panel of the LEC client end (20), and the LEC client end (20) is configured to send register data to the server (30) according to the profiles thereof. In one embodiment, a register protocol of the LEC client end (20) may include a register, a venue ID and a password.

After connecting with the server (30), the 3C client end (10) may not send further data to the server (30) before next connection, and may only receive data sent from the server (30) so as to check selected flash effect including colors, frequencies, and venue theme effects. It is noted that when sending the mentioned data of colors, frequencies and venue theme effects, the server (30) is configured to ensure the independence between different venues and prevent mutual interference. In one embodiment, a data protocol of the 3C client end (10) may include certain types of data including different colors, tempos, and venue theme effects. After connecting with the server (30), the LEC client end (20) may not receive further data from the server (30) before next connection, and may only send out data to the server (30). In one embodiment, the LEC client end (20) is configured to send the designated colors, frequencies, venue theme effects to the connected 3C client end (10) through the server (30). In another embodiment, a data protocol of the LEC client end (20) may include certain types of data including colors, tempos, venue theme effects, a venue ID, and a password.

Figure 2:
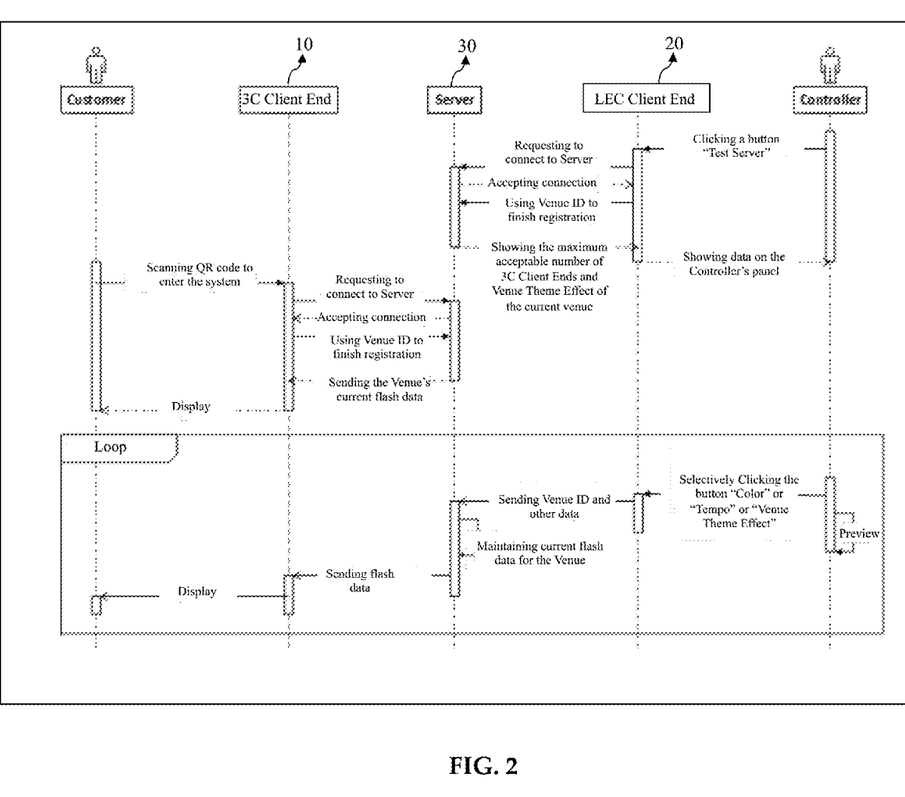
FIG. 2 is a schematic view of the communication between the 3C client end, the LEC client end and the server in the present invention.

Referring to FIG. 2, in one embodiment, the 3C client end (10), the LEC client end (20) and the server (30) are independently operated, and the server (30) is configured to synchronize with the 3C client end (10) or the LEC client end (20) only when receiving the register data to achieve high concurrency and stability. As a result, the server (30) is configured to have high processing speed when conducting and/or receiving a large amount of data. The server (30) may further include a color flash data buffer system which is configured to enable the 3C client end (10) and the LEC client end (20) to register at any time. More specifically, the 3C client end (10) or the LEC client (20) is configured to connect to the server (30) in a random order under a condition that a single venue is only connected and controlled by a single LEC client end (20) at one time. Moreover, the server (30) is configured to keep the latest connection of the LEC client end (20) at a single venue; i.e. once a new LEC client end (20) is connected to the server (30) at the same venue, the current LEC client end (20) is configured to be terminated and disconnected with the server (30).

Figure 3:
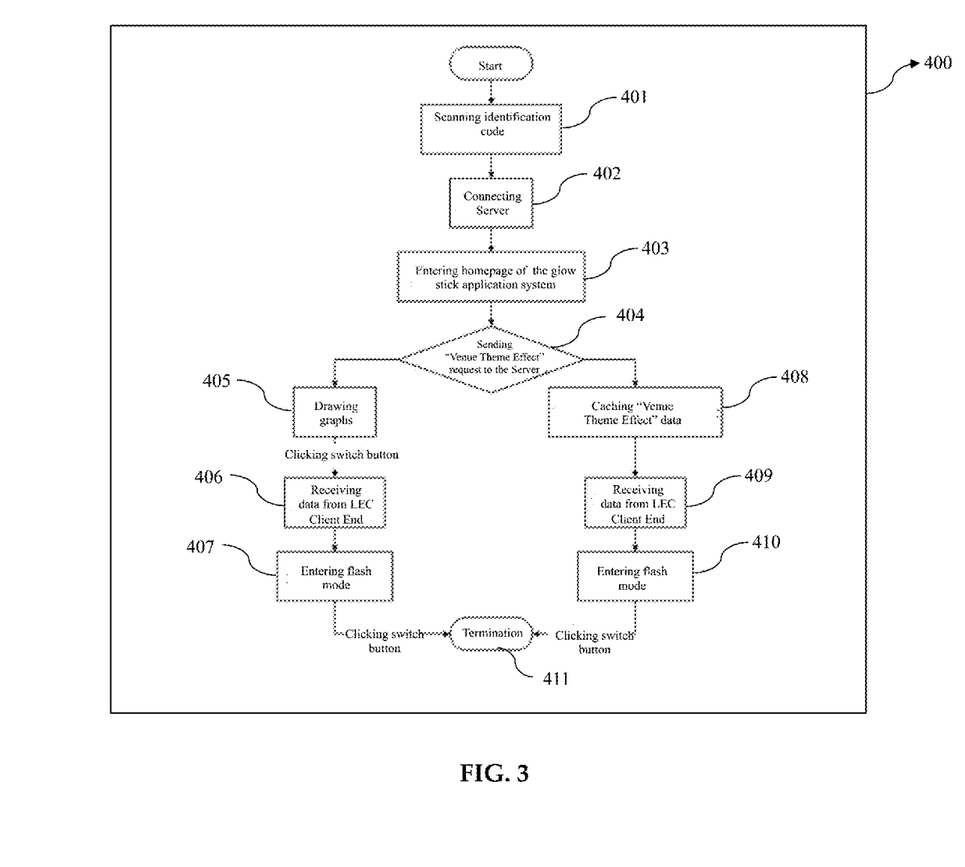
FIG. 3 is a flow diagram illustrating a controlling lighting effect on mobile devices from the 3C client end in the present invention.

Referring to FIG. 3, a method of controlling lighting effect on mobile devices from the 3C client end (10) may include following steps of scanning an identification code (401); connecting the 3C client end to the server (402); entering homepage of the lighting effect controlling system (403); and sending venue theme effect request to the server (404). In one embodiment, the identification code is a QR code. In another embodiment, if the 3C client end (10) wants to make his/her own graphics, the method may further include steps of the user drawing graphics (405); receiving data from LEC client end (406); and entering flash mode (407). In still another embodiment, if the 3C client end (10) wants to use a venue theme effect cached in the server (30), the method may further include steps of selecting a cached venue theme effect (408); receiving data from LEC client end (409); and entering flash mode (410). In both situations, the 3C client end (10) can click a switch button thereby terminating the flash mode (411). It is noted that the server (30) is configured to cache the flash data of the LEC client end (20) including colors, frequencies, and the current theme effects for next use.

For the 3C client end (10) with the Android operation system, the 3C client end (10) is configured to interpret the received data sent from the LEC client end (20) and start switching the flash characteristics including theme, color and frequency. In one embodiment, when a preferable theme, color or frequency is not found, the 3C client end (10) is configured to enter the homepage to draw his/her own graphics. Through clicking a tool button on the application, the 3C client end (10) is configured to select different sizes and colors of a pattern. After finishing the drawing, the 3C client end (10) can click the switch button on the application to start receiving the data from the LEC client end (20) and entering the flash mode. In one embodiment, the flash displaying on the 3C client end (10) can be terminated when the 3C client end (10) clicks the switch button again under the flash mode, and the 3C client end (10) can be re-directed to the homepage. When the 3C client end (10) exits the homepage, the connection between the 3C client end (10) and the server (30) may be terminated. Meanwhile, the server (30) can cache the data of previous connection in 12 hours. Through scanning the QR code again or clicking a button of continuing last connection, the 3C client end (10) is configured to connect to the same LEC client end (20) through the server (30) at the same venue in 12 hours, and the 3C client end (10) is configured to retrieve the last used flash data.

In one embodiment, for the 3C client end (10) with the Android operating system, the lighting effecting controlling system can be cooperated with the SurfaceView technique. The SurfaceView is provided a dedicated drawing surface embedded inside a view hierarchy; i.e. the SurfaceView can temporarily save unfinished graphics drawing by the 3C user in an internal memory and show a completed graphic on the screen once finished. In this way, the SurfaceView is configured to prevent screen flickering generated by repeatedly drawing on the screen. Also, it takes much longer for a central processing unit (CPU) of the 3C device to access a screen or a disk storage than a CPU cache or internal memory. Thus, through creating at least a buffer zone, the SurfaceView can increase efficiency of image processing. For example, the user is drawing five graphics on the screen, the graphics are can be saved in the buffer zone and be completely displayed on the screen once the user finished the drawing, which means that the CPU can access internal memory five times and only to access the screen one time which saves more time when the CPU may have to access the screen five times. In actual application, the SurfaceView has two buffer zones on the screen including a front buffer zone and a rear buffer zone. The user can draw a first graphic on the front buffer zone and continue to draw a second graphic on the rear buffer zone when the first graphic is processing, and through repeatedly and alternatively drawing on the two buffer zones, the drawing process can be more efficient. The SurfaceView is a preferred carrier for Android operating system when the system in the present invention needs to to display a number of graphics.

Moreover, for the Android operating system, the lighting effect controlling system in the present invention may include three kinds of animation classes, including Property Animation, View Animation, and Drawable Animation. Compared with the other two animation classes, the Property Animation is more preferable for the present invention and can repeatedly change a property of an object over a time period. As an animation, the object has at least a changeable property such as a position thereof. The Property Animation is configured to define four main properties of the animation including (1) duration; (2) time difference; (3) repeating times; and (4) animator sets. A core type of the Property Animation is called Value Animator which is used to complete the flash effect of graphics or lines. Through the animation classes, a user can design his/her own flash patterns of graphics by changing duration, time difference, repeating times or applying the animator sets.

Furthermore, the SurfaceView can be used to monitor the user's touch. For example, when the user uses his/her finger to slide on the screen of the connected 3C client end (10), the SurfaceView can record sliding coordinates and draw three lines which are overlapped. A first line located at a top portion of the three lines is a white line with the smallest width among the three lines, a second line located at a second portion of the three lines is wider than the first line, and a color thereof is sent by the LEC client end (20). A third line located at a bottom portion of the three lines is wider than the second line, and a color thereof is the same as the second line with an extent of ambiguity. After receiving the data from the LEC client end (20), the ValueAnimator can be operated to create an animation according to the width of the third line to create the flash effect thereof. In addition, the system in the present invention is configured to achieve the flash effect of graphic by changing different sizes of graphics.

For the 3C client end (10) with an iOS operating system, a 3C client end (10) is configured to access a homepage of the lighting effect controlling system in the same way as the Android operating system. The 3C client end (10) is configured to scan a QR code of a designated venue and send register data to the server (30). The QR code includes information of the corresponding LEC client end (20) including address, slogans and club id. After registration, the 3C client end (10) is configured to receive current flash data of the LEC client end (20) sent from the server (30) including color, frequency, and venue theme effect, and enter a theme mode. Thereafter, the 3C client end (10) is configured to click a switch button on a screen of the 3C client end (10) to start a flash mode, and the flash effect is configure to be changed according to instant messages sent from the LEC client end (20) through the server (30). As a result, when more than a 3C client end (10) scans the same QR code to connect to the corresponding LEC client (20) through the server (30), all of the 3C client ends (10) are configured to receive the same instant messages from the server (30) at the same time, to generate the synchronous effects. Also, the flash mode can be terminated by clicking the switch button again.

Figure 4:
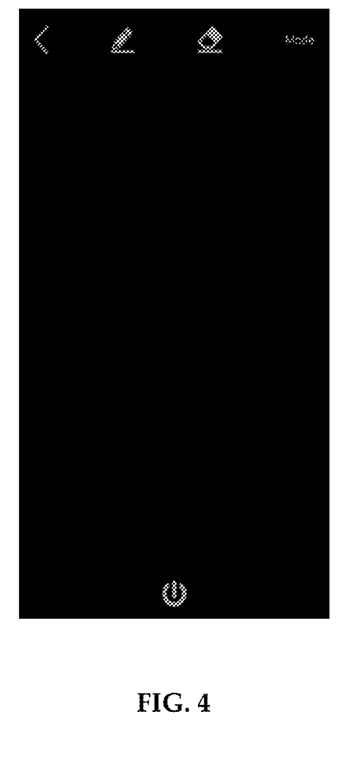
FIGS. 4 to 4d show the DIY mode in the present invention.
Figure 4A:
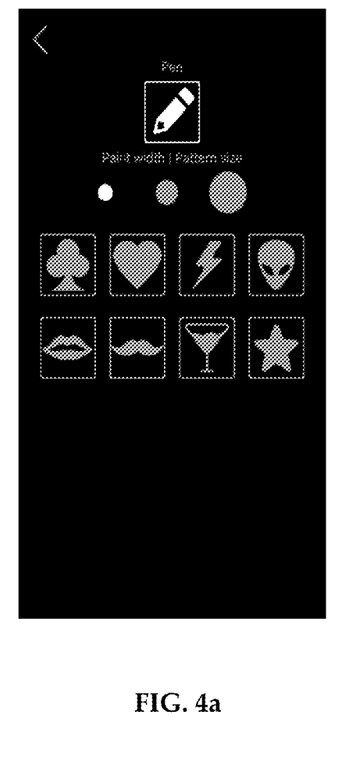
Figure 4B:
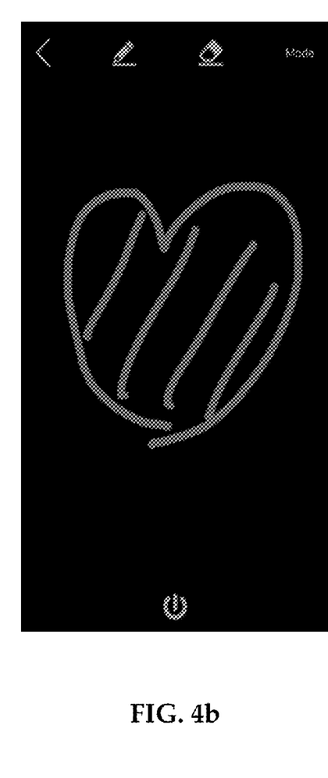

In another embodiment, the 3C client end (10) is configured to click a mode button to enter a DIY mode which enables the 3C client end (10) to draw different sizes of graphics and lines as shown in FIG. 4. The 3C client end (10) can pick the switch button to enter the flash mode after drawing, and the flash mode can be terminated by clicking the switch button again. Moreover, the 3C client end (10) can click a "drawing" button to enter an interface of selecting different sizes of pens or brushes. The "drawing" button may only be shown in the DIY mode. Also, in the DIY mode, the 3C client end (10) can select small, medium, or large graphic, or select thin, medium, or thick line as shown in FIG. 4*a*. The system can be auto-directed to the theme interface after selecting a designated graphic and/or line, and the 3C client end (10) can start drawing on a center portion of the screen as shown in FIG. 4*b*. During the drawing, the 3C client end (10) can use a clean button to clean the screen and re-draw if necessary.

Figure 4C:
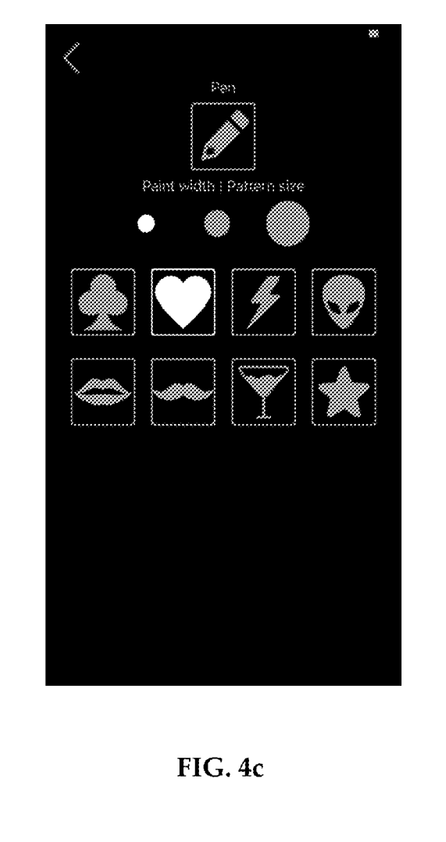
Figure 4D:
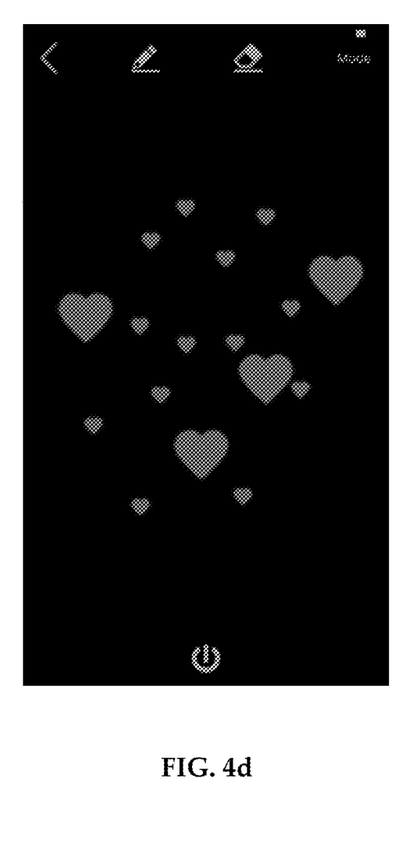

Instead of hand drawing, the 3C client end (10) can also select a predetermined pattern as shown in FIG. 4*c* and it can be shown on the 3C client end (10) as shown in FIG. 4*d*. It is noted that under the DIY drawing mode, the LEC client end (20) cannot direct and synchronize the theme pattern with the 3C client end (10), but the tempo and color.

For the iOS operating system, the lighting effect controlling system in the present invention can use "UIImageView" module as a canvas for drawing graphics or topic figures. The UIImageView can display a single image or a sequence of animated images in the interface and is cooperated with UIImage class which is configured to manage image data in the UIImageView. Also, the 3C client end (10) is configured to use an adapter pattern to select different brushes to draw graphics on the UIImageView, and the graphics can be overlaid, temporarily saved in UIImage, and timely updated on the screen of the 3C client end (10).

The flash principle for the iOS operating system is realized through overall blurring and superposition to process an original graphic to generate different flash effects. In one embodiment, after the 3C client end (10) clicks the switch button on the screen, the UIImageView is configured to successively process the transparent graphic on the canvas and generate seven graphics. The first graphic is the original graphic on the canvas, and the second graphic is processed by CIGaussianBlur blurry filter of CIFilter with a predetermined blurry radius of 2, and can be overlapped and on top of the first graphic. Similarly, the third graphic is processed by CIGaussianBlur blurry filter with a blurry radius of 4 and can be overlapped and on top of the first two graphics, and so on. Therefore, the seventh graphic is processed by CIGaussianBlur blurry filter with a blurry radius of 12 and can be overlapped on top of the first six graphics.

It is important to note that the size of the graphic may be changed after processed by the CIGaussianBlur blurry filter, and in order to have the graphics with the same size, the graphics may need to be cut before overlapped. The flash effect can be realized when the seven graphics are sequentially and repeatedly displayed with a predetermined time interval. In one embodiment, the time interval can be generated by the CADisplayLink timer which enables the system in the present invention to synchronize its graphics to a refresh rate of display. The iOS system has its Frame per Second (FPS) which is 60 Hz such that a selector of the CADisplayLink has a default run loop for 60 times per second. When the selector is called, the CADisplayLink can be used to record a last accumulated time (d) and a current time accurate down to a millisecond. Each of the last accumulated times (d) is accumulated to an accumulated time (t), and the screen can display a next flash graphic when a value of the accumulated time (t) is larger than the predetermined time interval.

Since the flash graphics are generated after drawn by the 3C client end (10) and the flash graphics cannot be changed during playing on the screen as an animation, the flash effect can be generated when the graphics are respectively displayed on the screen. Moreover, the iOS operating system is configured to temporarily save the graphics in an internal memory of the 3C client end (10), and the display time needs not to be recalculated during the flash process unless the server (30) sends out a message of changing colors to the 3C client end (10), thereby saving CPU and memory resources. However, in case that the server (30) sends out the message of changing colors to the 3C client end (10), the iOS end is configured to process color changing on the following four items: (i) current graphics on the canvas, (ii) the theme graphics, (ii) the seven flash graphics, and (iv) the current brush. As a result, the color of the graphics can be changed in the DIY mode, the flash mode, or a theme mode according to the message sent from the server (30).

Figure 5:
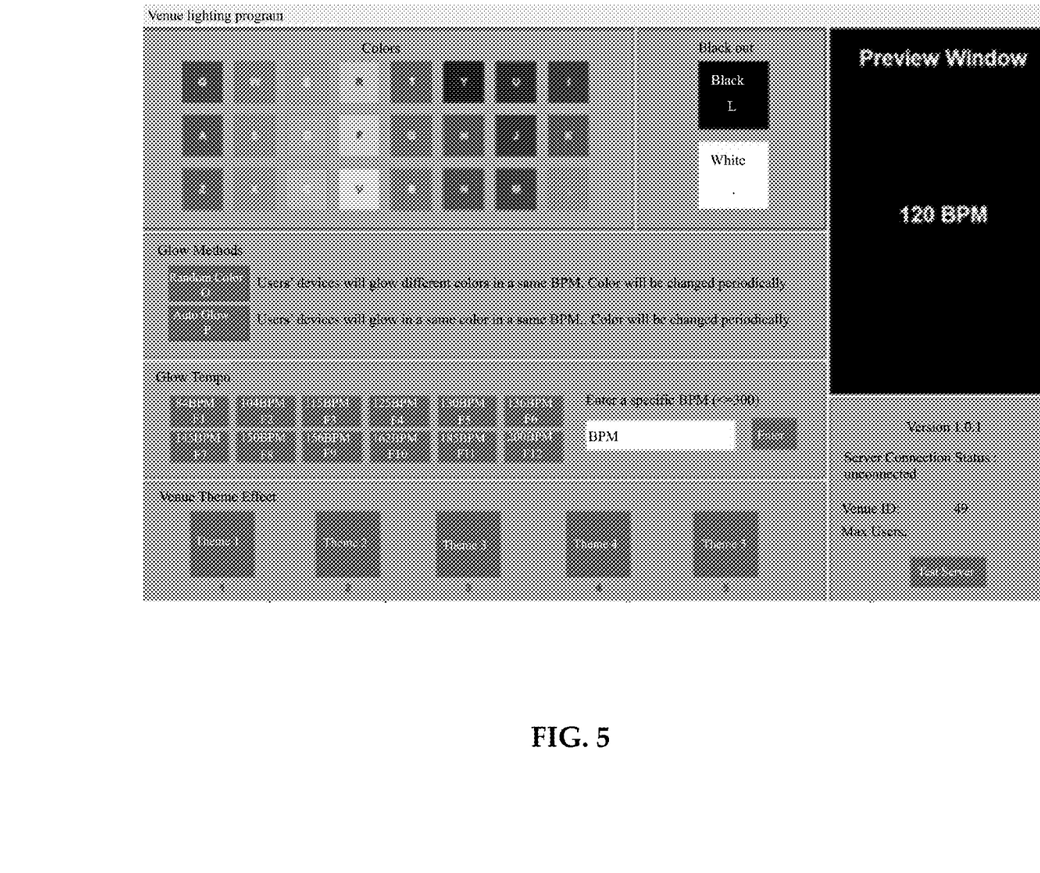
FIG. 5 is a schematic view of the LEC panel in the present invention.
Figure 5A:
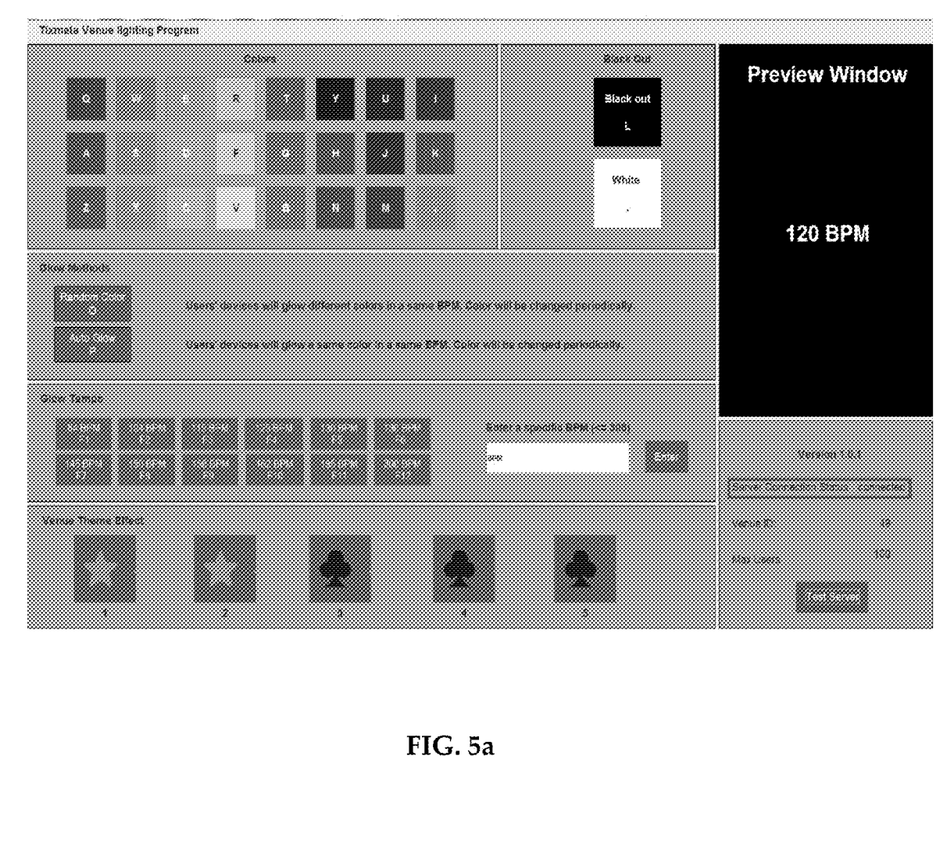
FIG. 5a is a schematic view of the LEC panel that is connected to the server.

Referring to FIG. 5, to the use of the LEC client end (20), the system in the present invention provides a LEC operating panel which is configured to be operated by a connected mouse or a connected keyboard. An interface of the LEC operating panel may include a preview window and a plurality of options including colors, frequencies having a maximum to 300 BPM, venue theme effects, and each of the options is configured to have an object shown thereon corresponding to a keyboard button. Thus, the LEC client end (20) can be easily operated and current flash effect of the venue can be shown. The LEC client end (20) can be connected to the server through the LEC operating panel as shown in FIG. 5*a*.

The LEC operating panel may have two special flash effects, Random Color and Auto Glow. The Random Color effect is configured to enable different 3C client ends (10) to have different flash colors with a synchronous flash frequency, and the Auto Glow effect is configured to enable the server (30) to auto-select colors with a synchronous flash frequency for the LEC client end (20) and change the color periodically. In one embodiment, the LEC client end (20) is can connect to the server (30) through a button of Test Server, and when the LEC client end (20) is successfully connected to the server (30), the LEC operating panel of the LEC client end (20) is configured to show a maximum acceptable number of 3C client ends (10) and 5 preselected venue theme effects of the current venue.

Also, the LEC operating panel is configured to show a connection status such as "connected" thereon for the LEC client end (20), and the LEC client end (20) can realize the corresponding flash effects through the options on the LEC operating panel. It is noted that when more than one LEC client end (20) is connected to the server (30) at the same venue, the current LEC client end (20) will be terminated and disconnected with the server (30) while a new LEC client end (20) will be connected to the server (30) to control the flash effects at the current venue. Meanwhile, the LEC operating panel of the terminated LEC client end (20) is configured to pop out a warming sign when the connection is terminated.

Figure 6:
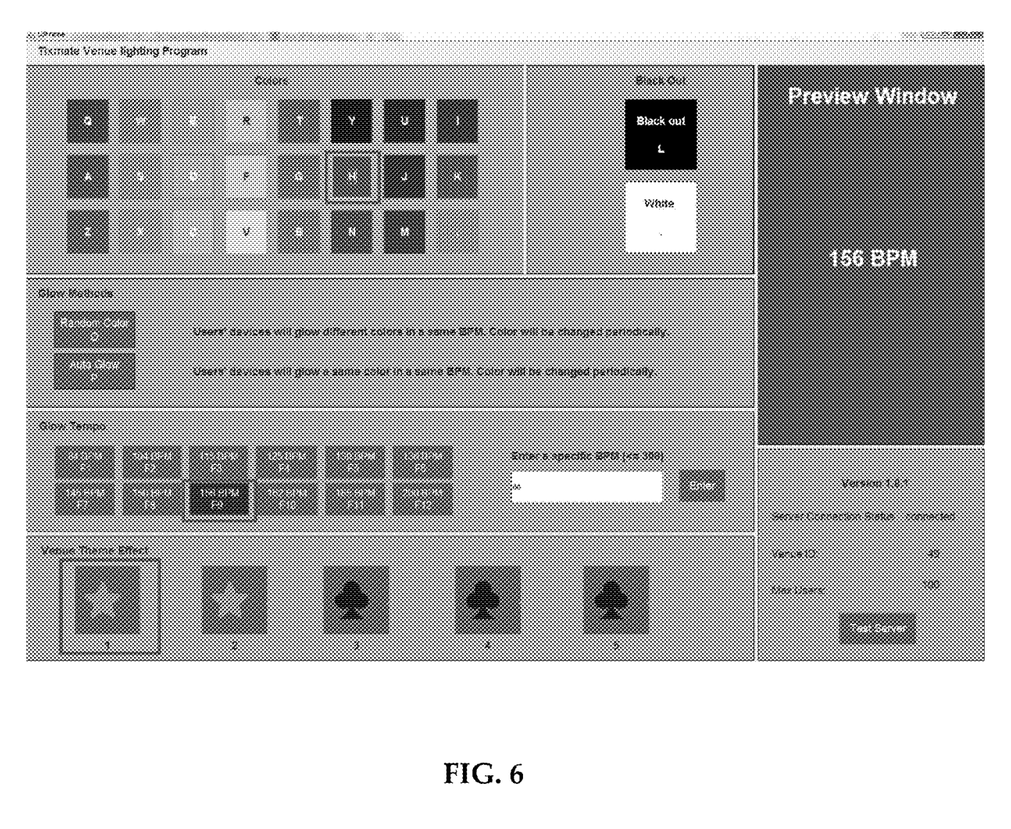
FIG. 6 is a schematic view of selecting a venue theme color and transmitting it to the 3C client end in the present invention.
Figure 6A:
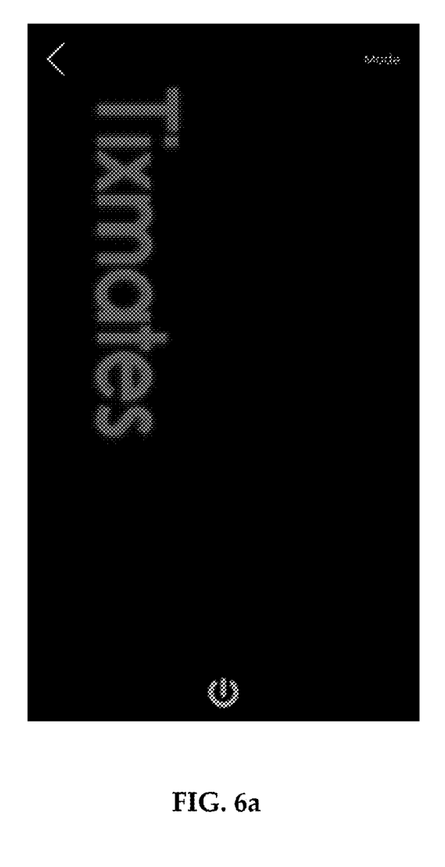
FIG. 6a is a schematic view of the 3C client end showing the venue theme color in the present invention.
Figure 7:
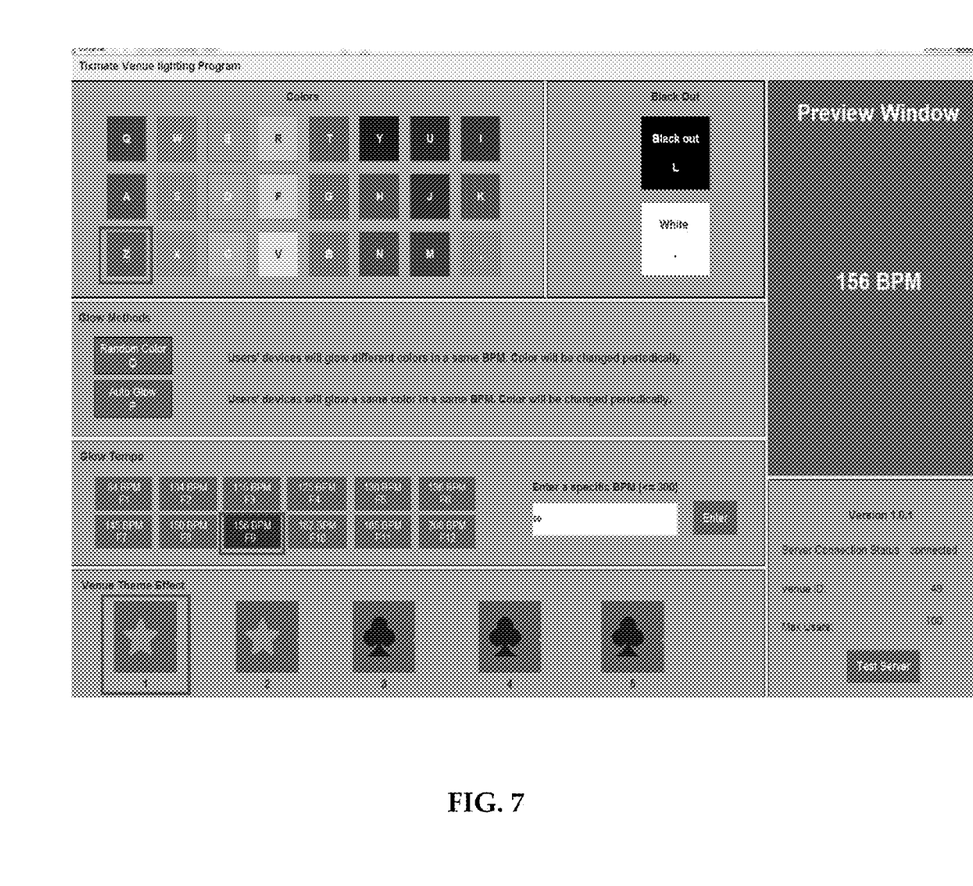
FIG. 7 is a schematic view of changing a venue theme color and transmitting it to the 3C client end in the present invention.
Figure 7A:
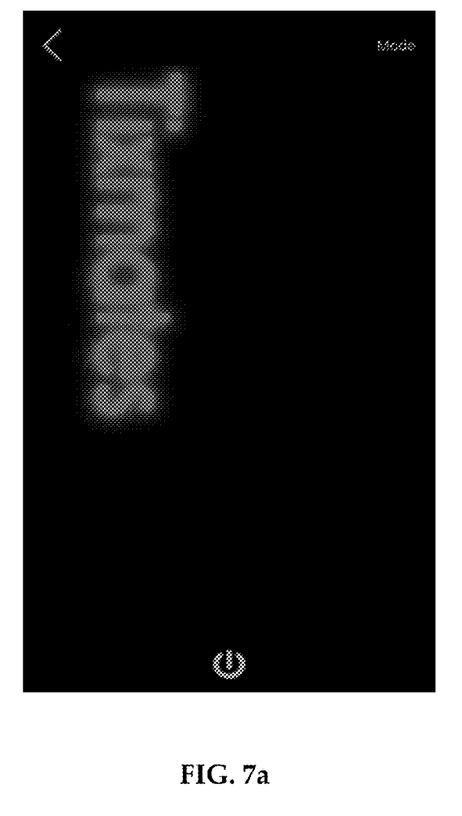
FIG. 7a is a schematic view of the 3C client end showing the new venue theme color in the present invention.

As shown in FIG. 6, current color of the venue is blue and such information will be transmitted to the server (30) and then to the 3C client end (10), so when the 3C client end (10) enters the venue, the venue theme color (blue) can be shown on the 3C client end (10) as shown in FIG. 6a. Similarly, when the venue theme color is changed from blue to pink as shown in FIG. 7, the color change can be transmitted to the server (30) then to the 3C client end (10) as shown in FIG. 7a. It is noted that the tempo and theme pattern are also changeable in the venue and the change can be similarly reflect on the 3C client end (10).

Figure 8:
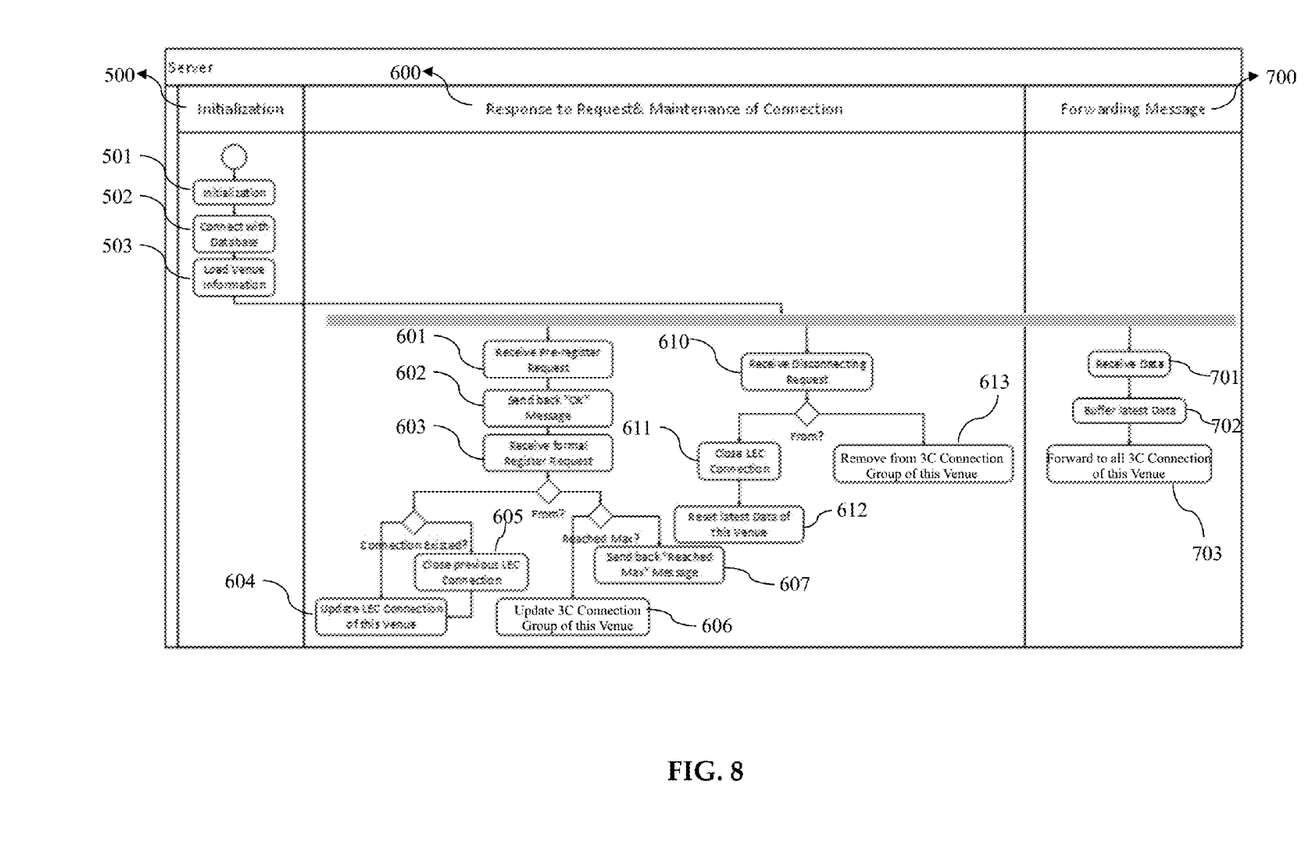
FIG. 8 is a flow diagram illustrating the functions of the server in the present invention.

In actual application, referring to FIG. 8, after initialization (500), the server (30) serves two main functions, including: (i) responding to the request and maintenance of connection (600); and (ii) forwarding the message (700). More specifically, the initialization of the server (30) includes following steps of executing the initialization (501); connecting with the database (502); and loading venue data (503). After initialization (500), the server (30) is configured to respond the requests from the 3C client end (10) and the LEC client end (20) and maintain the connection therebetween. In one embodiment, steps of responding request and maintenance of connection may include receiving pre-register request (601); sending back "ok" message (602); and receiving formal register request (603). In case that the formal register request is sent from the LEC client end (20), the server (30) is configured to check whether a connection of the LEC client end (20) at this venue exists, and when the connection of the LEC client end (20) does not exist, the server (30) is configured to execute a step of directly updating the LEC connection of this venue (604). On the other hand, if the connection of the LEC client end (20) does exist, the server (30) is configured to sequentially execute following two steps of closing previous LEC connection (605) and updating the LEC connection of this venue (604).

In another embodiment, if the formal register request is sent out from the 3C client end (10), the server (30) is configured to check whether a number of current connected 3C client ends (10) has reached the maximum acceptable number of this venue. In case that the maximum acceptable number of the 3C client ends (10) at the venue has not been reached, the server (30) can execute a step of accepting the request and updating the 3C client end (10) connection group of this venue (606). However, if the maximum acceptable number of the 3C client ends (10) at the venue has been reached, the server (30) is configured to execute a step of sending back a "Reached Max" message to the 3C client end (607). Moreover, the step of responding to request and maintenance of connection also include a step of receiving disconnecting request (610). In case that the server (30) receives the disconnecting request from the LEC client end (20), the server (30) is configured to sequentially execute two steps of closing LEC connection (611) and resetting latest data of this venue (612). However, if the server (30) receives the disconnecting request from the 3C client end (10), the server (30) can execute a step of removing from 3C connection group of this venue (613).

Additionally, the server (30) can receive data from the connected LEC client end (20) and forward the data to the connected 3C client ends (10) in this venue. The step (700) of forwarding the data to the 3C client ends may include steps of the server receiving data (701); buffering latest data (702); and forwarding to all 3C connection in this venue (703).

Moreover, for flash pattern, after receiving from the LEC client end (20), the server (30) can cache the flash pattern and send to the connected 3C client ends (20) in the venue. The server (30) can cache the latest data of flash pattern, and when a new 3C client end (10) is connected to the server (30), the 3C client end (10) can receive the latest date of flash pattern in a short period of time to achieve the synchronous effect at the venue. In one embodiment, for the new 3C client end (10), the server (30) can set the latest flash pattern as a default flash pattern.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A method of controlling lighting effects displayed on a plurality of mobile devices at a venue comprising steps of:
   providing predefined flash data for a corresponding venue through a lighting effect control (LEC) client end of the venue, the corresponding flash data comprising colors, frequencies (beats per minute) of display, and preselected optical venue theme effects to be displayed by the mobile device at the corresponding venue;
   connecting the LEC system to a server through an LEC operating panel;
   sending the flash data from the LEC client end to the server;
   storing the flash data at a database of the server;
   scanning an optical identification code at the venue by the mobile device;
   sending, by the mobile device, venue information obtained by the scanning, to the server;
   at the server, matching the obtained venue information to stored information;
   in response to the matching, sending, by the server, flash data corresponding to the venue, to the mobile device;
   displaying, by the mobile device, the flash data corresponding to the venue, in response to user activation on the mobile device;

sending instant messages from the server, at a same time, to a plurality of mobile devices at the corresponding venue that scanned the optical identification code, and in response, synchronously displaying flash data effects by the plurality of mobile devices at the corresponding venue based on the instant messages;

when matching is not performed by the server, creating, by users of the plurality of mobile devices, Do It Yourself (DIY) flash data through an interface provides on the plurality of mobile devices, the user flash data comprising colors, frequencies (beats per minute) of display, and preselected optical venue theme effects and/or user created drawings, and displaying, by the mobile device, the DIY flash data on the plurality of mobile devices, wherein at least the color and frequencies displayed by the plurality of mobile devices are synchronously displayed.

2. The method of controlling lighting effect on mobile devices of claim 1, wherein the identification code is a QR code.

3. The method of controlling lighting effect on mobile devices of claim 1, wherein the server is configured to cache the flash data of the LEC client end including colors, frequencies, and the current theme effects for next use.

4. The method of controlling lighting effect on mobile devices of claim 1, wherein the server is configured to cache the DIY flash data of the LEC client end including colors, frequencies, and the current theme effects for next use.

5. The method of controlling lighting effect on mobile devices of claim 3, wherein through scanning the identification code again or clicking a button of continuing last connection, the mobile device is configured to connect to the same LEC client end through the server at the same venue within a predetermined period of time, and the mobile device is configured to retrieve the last used flash data.

6. The method of controlling lighting effect on mobile devices of claim 4, wherein through scanning the identification code again or clicking a button of continuing last connection, the mobile device is configured to connect to the same LEC client end through the server at the same venue within a predetermined period of time, and the mobile device is configured to retrieve the last used DIY flash data.

\* \* \* \* \*